United States Patent [19]

Kojima et al.

[11] Patent Number: 5,585,469
[45] Date of Patent: Dec. 17, 1996

[54] DYEING AGENT HAVING AT LEAST TWO DYES FOR STAINING A BIOLOGICAL SAMPLE AND STAINING METHOD EMPLOYING THE DYEING AGENT

[75] Inventors: Yasuaki Kojima; Ryohei Yabe; Mitsuo Hattori; Kazumitsu Kawase, all of Katsuta, Japan

[73] Assignee: Hitachi, Ltd., Tokyo, Japan

[21] Appl. No.: 316,329

[22] Filed: Sep. 30, 1994

[30] Foreign Application Priority Data

Oct. 8, 1993 [JP] Japan ..................................... 5-252699

[51] Int. Cl.⁶ ..................... G01N 33/00; G01N 33/493; G01N 33/48; G01N 33/49
[52] U.S. Cl. ............................. 534/573; 8/639; 436/17; 436/63; 436/174; 436/805; 435/40.5; 435/40.51
[58] Field of Search ................... 436/17, 63, 174; 424/3, 7.1; 8/639; 534/573 M

[56] References Cited

U.S. PATENT DOCUMENTS

| | | |
|---|---|---|
| 3,822,095 | 7/1974 | Hirschfeld .................. 356/19 |
| 3,961,039 | 8/1976 | Sternheimer .................. 424/3 |

FOREIGN PATENT DOCUMENTS

| | | | |
|---|---|---|---|
| 259834 | 3/1988 | European Pat. Off. ................. 424/3 |
| 556971 | 8/1993 | European Pat. Off. ................. 356/19 |
| 57-500995 | 6/1982 | Japan ......................... 436/17 |
| 63-94156 | 4/1988 | Japan ......................... 436/63 |
| 5-040118 | 2/1993 | Japan ........................... 424/3 |
| 5-40118 | 2/1993 | Japan ........................ 436/174 |

OTHER PUBLICATIONS

Venkataraman, "The Chemistry of Synthetic Dyes", vol. VII, pp. 278–305 (1974).

D. Lapen, "A Standardized Differential Stain for Hematology", Cytometry, vol. 2, No. 5, Mar. 1982, pp. 309–315.

A. W. Krause et al, "Fluorescent Erythrosin B is Preferable to Trypan Blue as a Vital Exclusion Dye for Manmmalian Cells in Monolayer Culture", The Journal of Histochemistry and Cytochemistry, vol. 32, No. 10, Oct., 1984, pp. 1084–1090.

*Primary Examiner*—Floyd D. Higel
*Attorney, Agent, or Firm*—Fay, Sharpe, Beall, Fagan, Minnich & McKee

[57] ABSTRACT

Dyeing agents which are excellent in visual recognition of discernible or tangible components in a sample cause no coagulation of proteins, sugars or glycoproteins dissolved in the sample. An apparatus for image analysis of flow type stain particles uses the dyeing agents, and particles of discernible components suspended in a flowing sample can be detected so that images of the particles can be efficiently photographed and the discernible components can thus be analyzed by image processing of the thus-obtained image.

23 Claims, 7 Drawing Sheets

○: RED BLOOD CELL   ⊙: WHITE BLOOD CELL   ▨: EPITHELIAL CELL

DYEING AGENT HAVING AT LEAST TWO DYES FOR STAINING A BIOLOGICAL SAMPLE AND STAINING METHOD EMPLOYING THE DYEING AGENT

BACKGROUND OF THE INVENTION

1. Field of the Invention

The present invention relates to dyeing agents for the biological stain of red blood cells, white blood cells, epithelial cells or the like. In particular, the present invention relates to dyeing agents for bio samples like urine, containing extracellular tangible components such as crystals or casts; these components are difficult to discern from dye precipitates, urinary components deposited or coagulated, impurities such as dust, etc. which may be contained in the same biological sample, in addition to the aforesaid cellular components. The present invention also relates to a method for preparing such dyeing agents and to the use thereof.

The present invention further relates to an apparatus for particle image analysis in which images of particles suspended in flowing fluids are photographed and analyzed, and in particular, to an apparatus for analysis of particle images to determine the kind of cells or particles in blood or urine, or culture cells, etc. and the life or death of these cells.

2. Description of the Related Art

For classification and analysis of cells in blood or cells and particles in urine which have been employed in the prior art, a specimen is put on a glass slide and observed microscopically. In the case of urine having a low density of particles therein, a urinary sample is previously centrifuged with a centrifuging machine, and the thus-concentrated sample is microscopically observed. These operations for observation and inspection have been automated using an apparatus through the steps of applying the sample onto the glass slide, setting the glass slide in a microscope, automatically scanning a stage of the microscope to stop it at the position where particles are present, taking a picture of still images of the particles, and classifying the particles in the sample using characteristic extraction and pattern recognition techniques by image processing. However, such a process encounters problems in that it takes time for preparing a sample, and furthermore, additional operations are necessary for locating particles while mechanically moving the microscope stage and transferring the particles to an appropriate zone for image input. Thus, the time period for analysis is prolonged and the apparatus becomes complicated.

Flow cytometry for optically analyzing an analyte suspended in a fluid sample while flowing the sample in a flow cell is known. In flow cytometry, it is unnecessary to prepare a smear instead, a fluorescent or scattering intensity of each particle in a sample is determined. A flow cytometer has the ability to process 1000 particles per second. However, it is still difficult to obtain information which reflects morphological characteristics of particles. Flow cytometry is thus unable to classify particles by their morphological characteristics with the effective of microscopic observation.

An attempt has been made to take a photograph of particle images in a continuously flowing sample and analyze and classify the particles from the respective particle images; see Japanese Patent Application KOHYO No. 57-500995 and Japanese Patent Application KOKAI (Laid-Open) No. 63-94156.

Japanese Patent Application KOHYO No. 57-500995 discloses a method for analysis of particles which comprises passing a sample through a path in a special shape, flowing particles in the sample there in a wide zone for photographing, taking a picture of still images by a flash lamp, and analyzing the images. According to the method, the flash lamp, which is a pulse light source, periodically emits light by synchronizing with a CCD camera and, enlarged images of sample particles are projected on the CCD camera using a microscope. The emission time of the pulse light source is short so that still images can be obtained even though particles flow continuously. In addition, 30 sheets/sec of still images can be photographed with a CCD camera.

Japanese Patent Application KOKAI No. 63-94156 discloses a method which comprises providing a particle-detecting optical system other than a still image photographing system, upstream a zone for photographing particle images in a sample flow, previously detecting the passing particles at the particle detection zone, and flashing a lamp with an appropriate timing when the particles reach the zone for photographing particle images. According to this method, the passing particles can be detected without periodic emission of a pulse light source, and still images can be photographed only when the particles reach the photographing zone. Accordingly, particle images can be efficiently obtained. Even when a sample has a low concentration, there is no chance to process meaningless images where no particles are present.

On the other hand, when urinary sediments in urine are analyzed, microscopic observation is conventional without using any staining solution; only where it is difficult to distinguish an analyte is a dyeing agent for urinary sediments employed. For this technique, reference is made to, e.g., "KENSA-TO-GIJUTSU", Igaku Shoin Publishing Co., vol. 10, No. 9 (1982:9), 846–850, and Japanese Patent Application KOKAI No. 5-40118.

As listed in the above publications, conventional dyeing agents for urinary sediments include the Sternheimer dyeing agent, the New Sternheimer dyeing agent, the Sternheimer-Malbin dyeing agent, etc.

The Sternheimer dyeing agent consists of Solution I: 2% aqueous National Fast Blue solution, and Solution II: 1.5% aqueous Pyronin B solution. To prepare the dyeing agent, Solution I was blended with Solution II in a 1:1 ratio.

The New Sternheimer dyeing agent consists of Solution I: 2% aqueous Alcian Blue solution, and Solution II: 1.5% aqueous Pyronin B solution. To prepare the dyeing agent, Solution I was blended with Solution II in a ratio of 2:1.

The Sternheimer-Malbin dyeing agent consists of Solution I obtained by dissolving 3.0 g of Crystal Violet in 20.0 ml of 95% ethanol, adding 0.8 g of ammonium oxalate to the solution, and diluting the mixture with 80.0 ml of purified water; and Solution II obtained by dissolving 0.25 g of Safranine O in 10.0 ml of 95% ethanol and diluting the solution with 100.0 ml of purified water. To prepare the dyeing agent, Solution I was blended with Solution II in a ratio of 3:97.

In flow cytometry in which urinary sediments in continuously flowing urine are photographed and the sediments are analyzed and classified from the respective images of the sediments, improvement in image processing efficiency depends on cutting-out of images to be analyzed, extraction of characteristic parameters such as color, shape, size, etc. It is thus required to stain the analyte for improving the image processing efficiency.

Staining for urinary sediments using the conventional Sternheimer dyeing agent and New Sternheimer dyeing agent is a highly useful method for supravital staining which is excellent in visual recognition of sediment components in urine.

However, these dyeing agents consist of polar molecules in which charges in the constituent dye molecules are localized. As a result, when dyeing agents are mixed with urine, agglutination of proteins, sugars, glycoproteins, etc. dissolved in urine is caused to form the agglutination products. For this reason, when it is attempted to photograph particle images of urinary sediments stained with these dyeing agents, the agglutination products interfere as impurities to seriously reduce the detection efficiency of urinary sediments or cause clotting of the flow path. Furthermore, depending upon the agglutination products, their shape might be misread as casts; or where cells, casts or blood cells are hidden in an agglutination mass, these components might be overlooked.

In addition, flow cytometry involves a problem that hemolysis results in an inaccurate count of red blood cells. Furthermore, the agglutination products which should be discarded are also labeled in a step of image processing so that the speed of classification processing decreases or image memory capacity becomes insufficient.

On the other hand, staining for urinary sediments using the Sternheimer-Malbin dyeing agent is inferior in visual recognition of discernible components in urine to the aforesaid staining. In addition, tyrosine-like needles are sometimes formed and might be misread as crystals derived from urine. Furthermore, the Sternheimer-Malbin dyeing agent involves a serious problem in that the count of red blood cells becomes inaccurate due to hemolysis caused by the dyeing agent, as in the staining described above.

As stated above, the conventional dyeing agents could not provide any satisfactory results in an apparatus for image analysis of flow type stain particles in which an analyte component in a continuously flowing sample is photographed to perform image analysis.

SUMMARY OF THE INVENTION

An object of the present invention is to solve the foregoing technical problems and provide a dyeing agent having advantages, which causes no agglutination of dyes in the agent, causes no coagulation of the proteins, sugars, glycoproteins, etc. dissolved in urine, causes no hemolysis but is excellent in visual recognition of discernible components in urine, enables to accurately count red blood cells and is also suited for image processing.

Another object of the present invention is to provide an apparatus for analysis and classification of urinary sediment components in which, when urinary sediments in continuously flowing urine pass through a zone for detecting particles in a flow cell, the urinary sediments are efficiently photographed while detecting the particles, and the thus-obtained images of the sediments are subjected to image processing. In order to eliminate the prior art problems caused by using the conventional dyeing agents, the urinary sediments are stained with the aforesaid dyeing agent of the present invention and the sediment images are then image processed.

Therefore, the present invention relates to a dyeing agent for staining a biological sample, which comprises at least two dyes for staining cells and tissue, and a pH buffer, said dyes being nonpolar molecular dyes which, upon blending, cause no agglutination or sedimentation and which do not precipitate or agglutinate sugars, proteins or glycoproteins dissolved in said biological sample. The dyes stain at least two objects for staining to different degrees in color hue or in dyeing strength depending on the respective objects, and stain, in the case of the same object for staining, the respective components constituting the object to different degrees in color hue or in dyeing strength.

The present invention also relates to an apparatus for image analysis of flow type stain particles, comprising a flow cell for flowing particles suspended in a fluid sample, means for detecting the particles which pass through a zone for detecting the particles in the flow cell, means for photographing a still image of the detected particles in the flow cell which passed through the photographing zone, and a means for image processing the particle image photographed for morphological classification, wherein said apparatus further comprises a staining mechanism comprising a dyeing agent for staining the particles, a bottle for the dyeing agent, a mechanism for supplying the dyeing agent and a staining tank.

PREFERRED EMBODIMENTS OF THE INVENTION

The dyeing agent of the present invention comprises dyes for staining cells and tissues, a pH buffer, and a stabilizing agent. The dyes for staining cells and tissues comprise a plurality of nonpolar molecular dyes for staining. Even when these dyes are blended, the dyes do not react with each other, do not cause agglutination or sedimentation, do not precipitate or agglutinate the dissolved sugars, proteins or glycoproteins in the biological sample, and can stain, in the case of a plurality of objects to be stained, to different degrees of hue or dyeing strength depending on the respective objects, and which can stain, in the case of the same object for staining, the respective components constituting the object to different degrees of hue or dyeing strength.

The apparatus for image analysis of the present invention performs morphological classification of particles by causing particles suspended in a fluid sample to flow into a flow cell, detecting the particles which pass through a zone for detecting the particles in the flow cell, photographing a still image of the detected particles in the flow cell which have passed through the photographing zone, and analyzing the particle image photographed.

The dyes for staining are preferably azo dyes and xanthene dyes used for supravital staining.

As the azo dyes, either Evans Blue or Trypan Blue is preferred.

As the xanthene dyes, either Erythrosine, Phloxine or Eosin is preferred.

The pH buffer is preferably a phosphate buffer, a succinate buffer or a tris-acid buffer.

The dyeing agent of the present invention may contain a stabilizing agent. The stabilizing agent is preferably an antibacterial agent. As the antibacterial agent, preferred is sodium azide, para-hydroxyphenylacetic acid, dehydroacetic acid or ethylenediaminetetraacetic acid.

The dyeing agent of the present invention is prepared as follows. One volume of about 0.2 to $10.0 \times 10^{-2}$ mol/l of Evans Blue or Trypan Blue is blended with about 0.5 to 2.0 volumes of about $0.2$ to $10.0 \times 10^{-2}$ mol/l of Erythrosine. At this stage, it is preferred to adjust pH to 5.7–7.9 using as a solvent 1/30 to 1/5 mol/l of a phosphate buffer, a succinate buffer or a tris-acid buffer. Sodium azide, para-hydroxyphenylacetic acid, dehydroacetic acid or ethylenediaminetetraacetic acid may be added to the solution mixture of Evans Blue or Trypan Blue and Erythrosine in a concentration of about 0.01 to 1.0%.

Where Phloxine which stains the object and at the same time destroys the object is selected as the xanthene dye, a fixative agent is incorporated into the dyeing agent so that the object can be stained without destruction. Such a dyeing agent can be prepared as follows. That is, 1 volume of about 0.2 to $10.0 \times 10^{-2}$ mol/l of Evans Blue or Trypan Blue is blended with about 0.5 to 2.0 volumes of about 0.2 to $10.0 \times 10^{-2}$ mol/l of Phloxine. Then, sodium azide, para-hydroxyphenylacetic acid, dehydroacetic acid or ethylenediaminetetraacetic acid may be optionally added to the solution mixture in a concentration of about 0.01 to 1.0%. Thereafter, the pH is adjusted to 5.7–7.9 using as a solvent 1/30 to 1/5 mol/l of a phosphate buffer, a succinate buffer or a tris-acid buffer. Finally glutaraldehyde, formaldehyde or paraformaldehyde is added as the fixative agent to the mixture in a concentration of 0.02 to 5.0%.

Where Eosin having a low staining specificity is selected as the xanthene dye, a surface active agent and a fixative agent are incorporated into the dyeing agent so that non-uniform staining can be prevented and the object can be stained without destruction of the object. Such a dyeing agent can be prepared as follows. One volume of about 0.2 to $10.0 \times 10^{-2}$ mol/l of Evans Blue or Trypan Blue is blended with about 0.5 to 2.0 volumes of about 0.2 to $10.0 \times 10^{-2}$ mol/l of Eosin. Then, sodium azide, para-hydroxyphenylacetic acid, dehydroacetic acid or ethylenediaminetetraacetic acid may be optionally added to the solution mixture in a concentration of about 0.01 to 1.0%. Thereafter, the pH is adjusted in a range of 5.7 to 7.9 using as a solvent 1/30 to 1/5 mol/l of a phosphate buffer, a succinate buffer or a tris-acid buffer. Finally glutaraldehyde, formaldehyde or paraformaldehyde as the fixative agent and sodium dodecyl sulfate as the surface active agent are added to the mixture, respectively, in a concentration of 0.02 to 5.0% and in a concentration of 0.01 to 0.5%.

The objects for staining in a biological sample are preferably discernible components in urinary sediments or in blood, cells or culture cell components.

The composition of the dyeing agent for staining urinary sediments according to the present invention was determined as follows. The dyeing agent was prepared as follows.

About 40 dyes having a structure in which charges are not considered to be localized in the molecule were selected from those used for staining cells and tissue, such as azine dyes, xanthene dyes, azo dyes, thiadiazine dyes, triphenylmethane dyes, etc. After 200 µl of urine collected from a healthy donor was added to 80 µl a of staining solution prepared in a concentration of $6.3 \times 10^{-3}$ mol/l, microscopic observation was made to examine if agglutination of dissolved proteins, sugars, glycoproteins or the like occured. As a result, the 13 dyes (6 red dyes and 7 blue dyes) shown in Table 1 were found. Table 1 is a list of the dyes that do not cause agglutination of the matters dissolved in urine as the result of cell and tissue staining tests. In Table 1, Color Index Number is abbreviated as C.I. No.

TABLE 1

| No. | Dye | C.I. No. | Peak Wavelength (nm) |
| --- | --- | --- | --- |
| 1 | Neutral Red | 50040 | 530.6 |
| 2 | Eosin Y | 45380 | 516.4 |
| 3 | Phloxine B | 45410 | 538.2 |
| 4 | Erythrosine | 45430 | 526.4 |
| 5 | Congo Red | 22120 | 498.2 |
| 6 | Azocarmin GFM | 50085 | 523.4 |
| 7 | Methylene Blue | 52015 | 590.0 |
| 8 | Evans Blue | 23860 | 608.0 |
| 9 | Azure B | 52010 | 646.4 |
| 10 | Methyl Green | 42590 | 632.0 |
| 11 | Fast Green FCF | 42053 | 623.0 |
| 12 | New Methylene Blue N | 52030 | 590.2 |
| 13 | Trypan Blue | 23850 | 599.0 |

Next, according to the matrix shown in Table 2, microscopic observation was made to see if sediments are formed due to agglutination of red dyes in combination with blue dyes. Staining solutions, each of which was prepared in a concentration of $6.3 \times 10^{-3}$ mol/l, were blended by 50 µl each. It was thus confirmed that 25 combinations of the dyes shown by ○ or ⊙ did not form sediments or crystals inherent to the dyes. Table 2 shows the results of whether or not precipitates were formed in the combination of dyes, wherein symbols indicate:

x precipitates were formed

○ no precipitates were formed

⊙ no precipitates were formed and cell staining was good

TABLE 2

| | Red Dye | | | | | |
| --- | --- | --- | --- | --- | --- | --- |
| Blue Dye | Neutral Red | Eosin Y | Phloxine B | Erythrosine | Congo Red | Azocarmine GFM |
| Methylene Blue | ○ | x | x | x | x | x |
| Evans Blue | ○ | ⊙ | ⊙ | ⊙ | ○ | ○ |
| Azure B | ○ | ○ | ○ | ○ | x | ○ |
| Methyl Green | ○ | x | x | x | x | x |
| Fast Green | x | ○ | ○ | ○ | ○ | ○ |
| New Methylene Blue | ○ | x | x | x | x | x |
| Trypan Blue | ○ | ○ | ○ | ⊙ | ○ | ○ |

Figure 1:
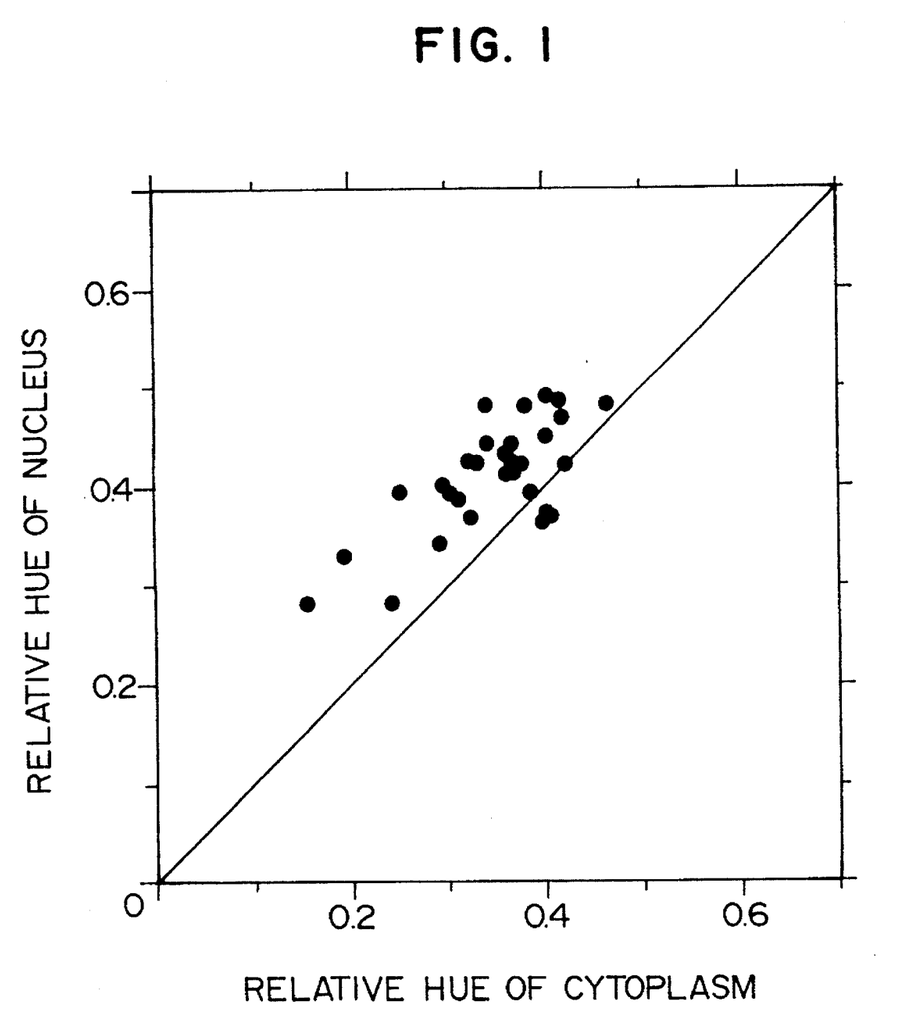
FIG. 1 is a diagram showing relative color hues of cytoplasm and relative color hues of a nucleus.

In order to obtain some combinations having good staining out of the 25 combinations above, 80 µl of a staining solution was mixed with 200 µl of urine from a healthy donor to see if the nucleus and cytoplasm of epithelial cells were distinctly stained. As a result, good staining was obtained in the four combinations shown by symbol ⊙ in Table 2 above. FIG. 1 is a diagram showing relative color hues of cytoplasm and relative color hues of nuclei. In FIG. 1, a ratio of the peak of Evans Blue to the peak of Erythrosine is shown by measuring the color hue of the nucleus and cytoplasm of epithelial cells with a microscope spectrometer having a lighting spot, of about 2 μm when stained with the combination of Evans Blue and Erythrosine. It was confirmed by the test that the dyeing agent of the present invention dyes the nucleus to blue and the cytoplasm to red.

When Trypan Blue is used instead of Evans Blue, similar results are obtained.

Two combinations of Evans Blue and Erythrosine, and Evans Blue and Phloxine were selected from the four combinations of dyes which showed a good staining property, and compared to the New Sternheimer dyeing agent and the Sternheimer-Malbin dyeing agent with respect to coagulation of matter (proteins, sugars, glycoproteins, etc.) dissolved in urine. After 400 μl of each staining solution described below was mixed with 1 ml of urine from a healthy donor, the number of particles was counted with a particle counter. The composition of each staining solution is as follows.

Dyeing Solution 1 . . . Sternheimer-Malbin dyeing agent

Dyeing Solution 2 . . . Evans Blue and Phloxine

Dyeing Solution 3 . . . Evans Blue and Erythrosine

Dyeing Solution 4 . . . New Sternheimer dyeing agent

As a control solution, was used 400 μl of physiological saline was used.

Figure 2:
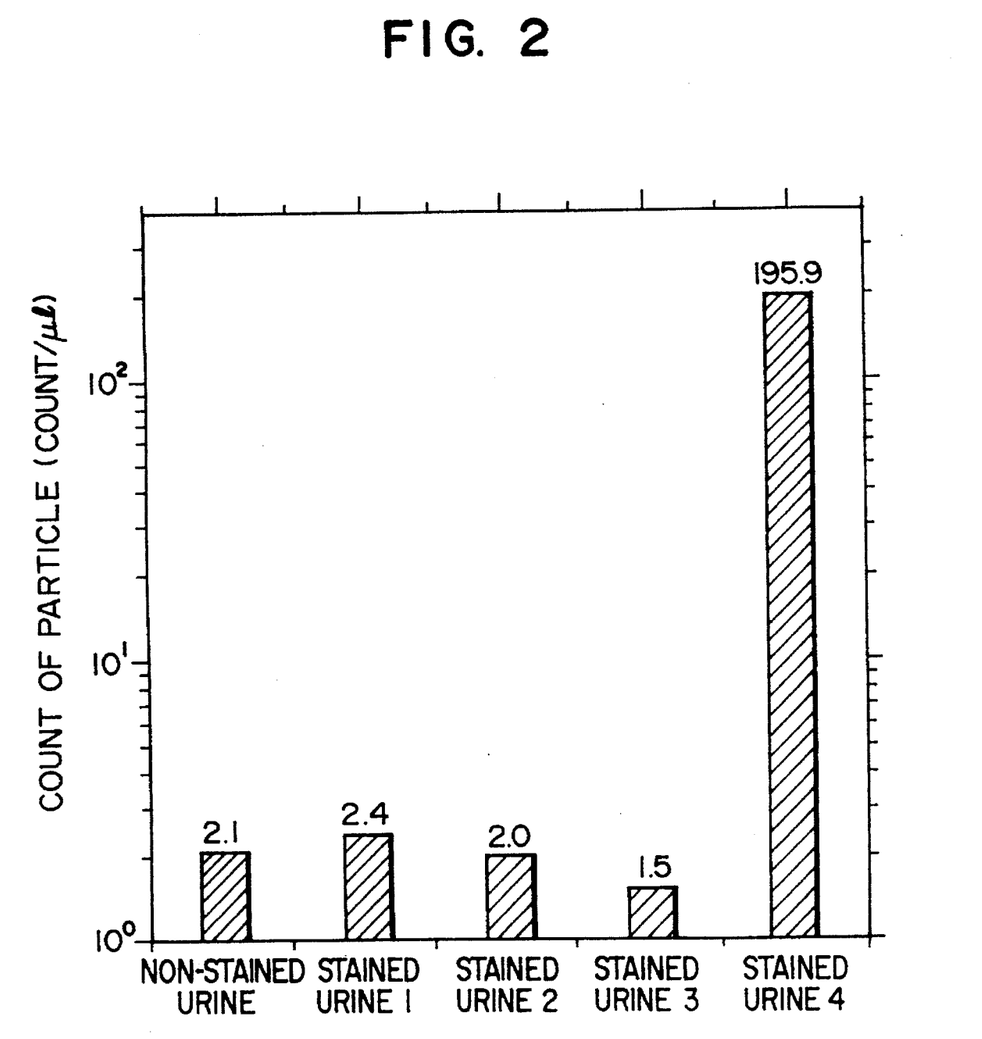
FIG. 2 is a diagram showing the relationship between stained urine and agglutination products in the urine.

Urine from a healthy donor which was stained with Staining solutions 1 through 4 are designated Stained Urine 1 to 4, respectively. FIG. 2 is a diagram showing the relationship between stained urine and agglutination products in the urine. As shown by the bar graph of FIG. 2, the count of urine stained with the New Sternheimer dyeing agent showed 196 particles/μl, namely, 90 times the count (2 particles/μl) of nonstained urine; it was thus confirmed that the matters dissolved in urine were coagulated. On the other hand, it was confirmed that the two combinations, Staining solutions 2 and 3, described above caused no coagulation (the count was 2 particles/μl in both cases), though the dyeing property was comparable to that with the New Sternheimer dyeing agent. Similar results were also obtained by using Trypan Blue in place of Evans Blue. In order to improve the dyeing ability of the Sternheimer-Malbin dyeing agent, the amount of the dyeing agent was increased. It was confirmed that the matter dissolved in urine was coagulated and that undesired coagulation increased with the increased amount of the dyeing agent.

Figure 3:
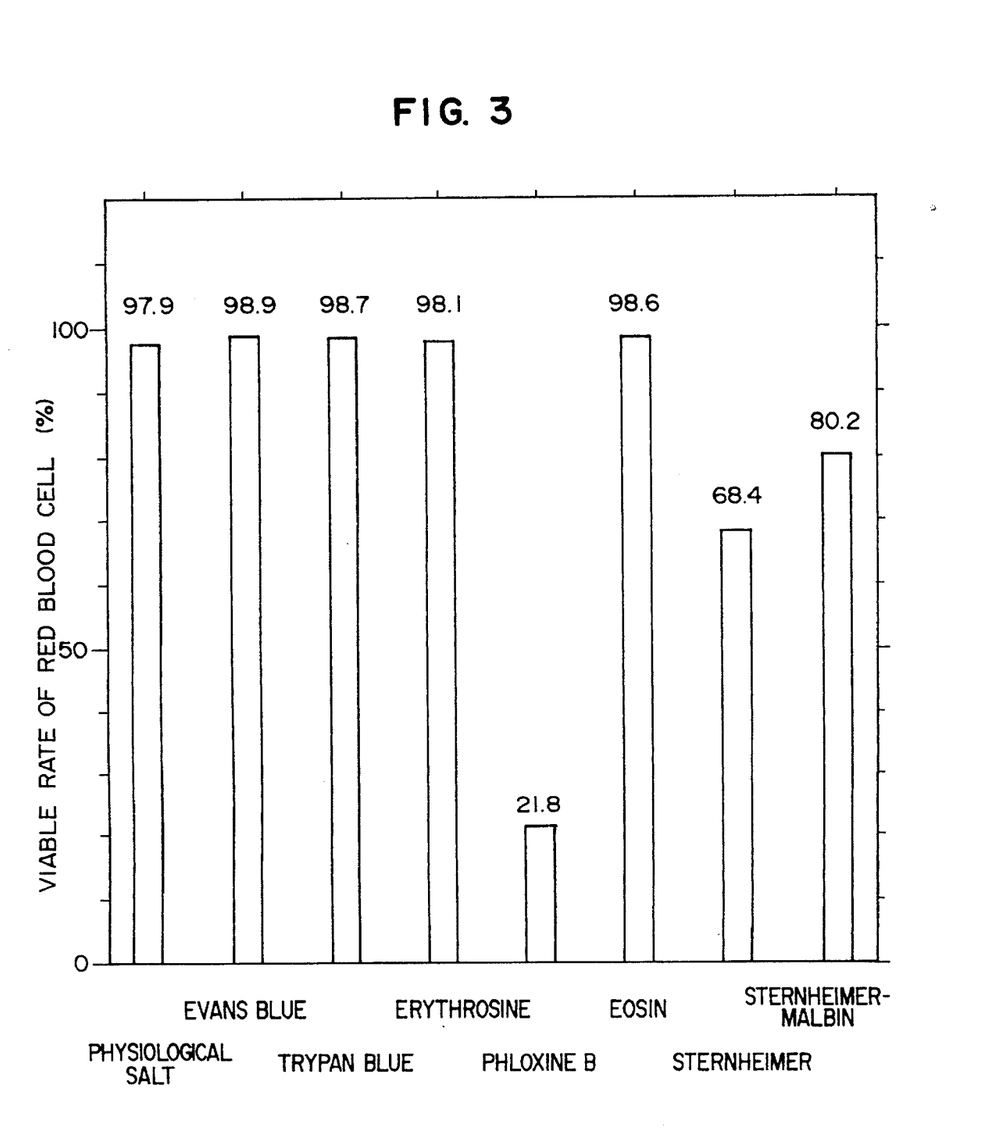
FIG. 3 is a diagram showing the relationship between each dyeing agent and a viable rate of red blood cells.
Figure 4:
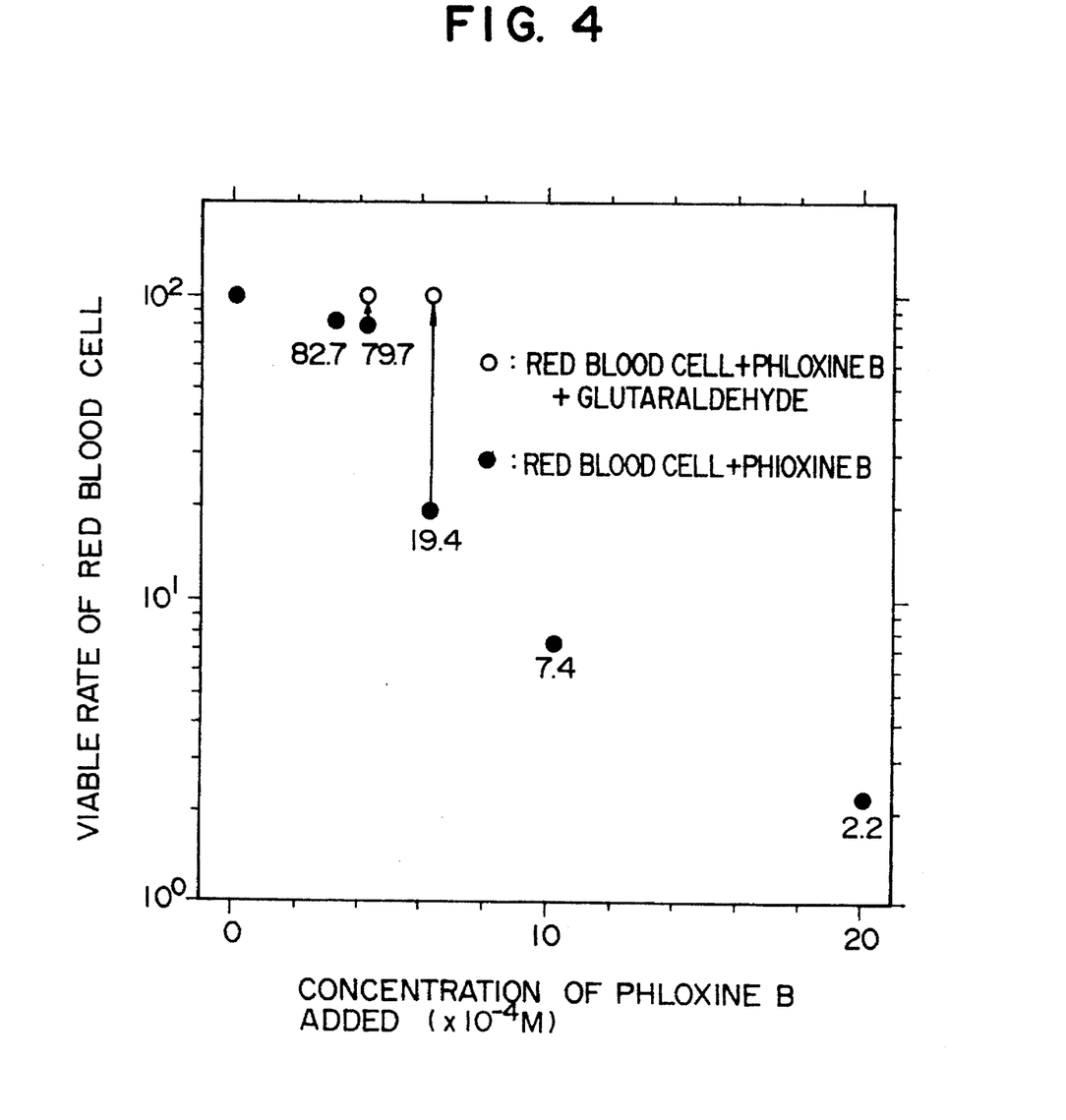
FIG. 4 is a diagram showing a viable rate of red blood cells when a fixative agent is added to Phloxine.

To examine the effect of the dyeing agents on red blood cells, 400 μl each of Trypan Blue, Evans Blue, Erythrosine, Phloxine, Eosin, the Sternheimer dyeing agent and the Sternheimer-Malbin dyeing agent was added to 1 ml of a sample obtained by adding whole blood collected from a healthy donor to physiological saline, and red blood cells free of hemolysis were counted with a Fuchs-Rosenthal hemacytometer. FIG. 3 is a diagram showing the relationship between each dyeing agent and the viable rate of red blood cells. As shown by the bar graph of FIG. 3, it was confirmed that the hemolysis was noted with Sternheimer dyeing agent, Sternheimer-Malbin dyeing agent and Phloxine, but other dyes showed no hemolysis. With regard to Phloxine, glutaraldehyde was added in a concentration of 3% for the purpose of maintaining the shape of red blood cells. FIG. 4 is a diagram showing the viable rate of red blood cells when the fixative agent was added to Phloxine. As shown in FIG. 4, the fixative agent markedly prevented hemolysis.

In the combination of either Evans Blue or Trypan Blue and Eosin which has a little low staining ability, sodium dodecyl sulfate was added in a concentration of 0.1% for the purpose of improving the staining ability. It was visually confirmed by microscopic observation that various discernible components were stained uniformly. In this case, 3% of glutaraldehyde was added to maintain the shape of red blood cells.

The dyeing agent in accordance with the present invention, when mixed with, e.g., urinary sediments or a urine sample prior to centrifugation, can stain specifically and selectively discernible components only to provide stain patterns having a good visual recognition property.

Figure 5A:
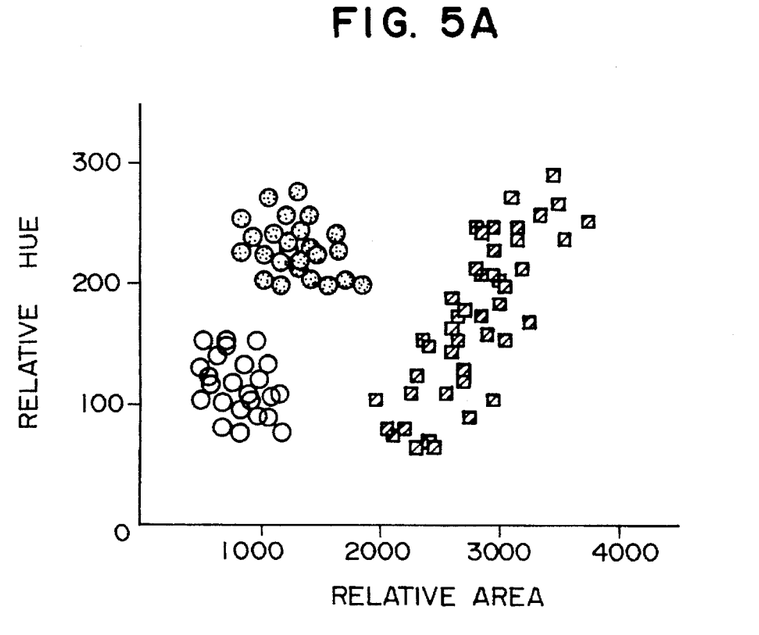
FIG. 5A and FIG. 5B are each a diagram showing relative areas of the images obtained and relative hues of the images.
Figure 5B:
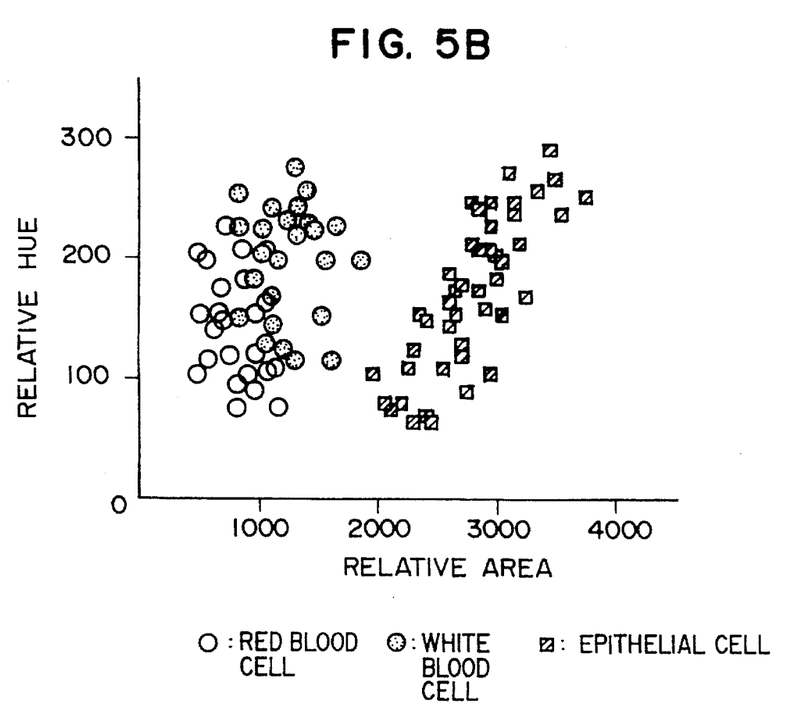

FIG. 5A and FIG. 5B are diagrams showing relative areas of images cut-out by image processing and relative hues of the images.

Urinary sediments stained with the combination of Trypan Blue and Erythrosine in FIG. 5A and urinary sediments stained with the Sternheimer-Malbin dyeing agent in FIG. 5B are are caused to flow in a flow cell to detect the urinary sediments passing through a particle detection zone in the flow cell. When the urinary sediments pass through a photographing zone in the flow cell, still images of the urinary sediments are photographed efficiently, and the thus-obtained images of the urinary sediments are subjected to image processing thereby to extract the characteristic patterns and obtain the relationship between relative areas of the objective images and relative color hues of the images. As shown in FIG. 5A and FIG. 5B, it has been confirmed that the dyeing agent in accordance with the present invention can distinctly stain the urinary sediments to different degrees of color hue and dyeing strength, depending on the kinds thereof, so that characteristic parameters effective for image processing can be provided.

In addition, the dyeing agent in accordance with the present invention does not coagulate sugars, proteins, glycoproteins, etc. dissolved in urine so that the dyeing agent can prevent clotting in the pass system due to coagulated matter. Furthermore, the dyeing agent does not give any incorrect detection due to coagulated matter so that urinary sediments can be efficiently detected and images of the urinary sediments can be accurately photographed.

Further, in the step of image processing, the time period for processing which might be additionally required by coagulated matter can be shortened, and the image memory capacity can be ensured.

The coagulated matter might be incorrectly taken as casts depending on their shape or might incorporate various discernible components such as cells, casts, blood cells, etc. into a coagulation mass to cause inconsistency between the actual number and the counted number. The dyeing agent of the present invention can get rid of such problems.

Furthermore, by selecting dyes that do not cause crystals derived from a staining solution or by selecting the combination of dyes, which mixture does not cause sediments, occurrence of artifacts derived from a staining solution can be prevented and distinct recognition of extracellular components present in a sample can be more precise.

Further, by selecting dyes that are not accompanied by hemolysis, red blood cells can be prevented from hemolysis; alternatively, hemolysis of red blood cells may also be prevented by adding a fixative agent to dyes having hemolysis.

Where dyes having a low dyeing ability are employed, addition of a surface active agent can prevent non-uniform dyeing to improve the dyeing ability.

According to the apparatus for image analysis of flow type stain particles of the present invention, the components of urinary sediments can be analyzed and classified based on images of the urinary sediments by photographing images of the urinary sediments while detecting particles when the urinary sediments have continuously flown pass through the particle detection zone.

Figure 6:
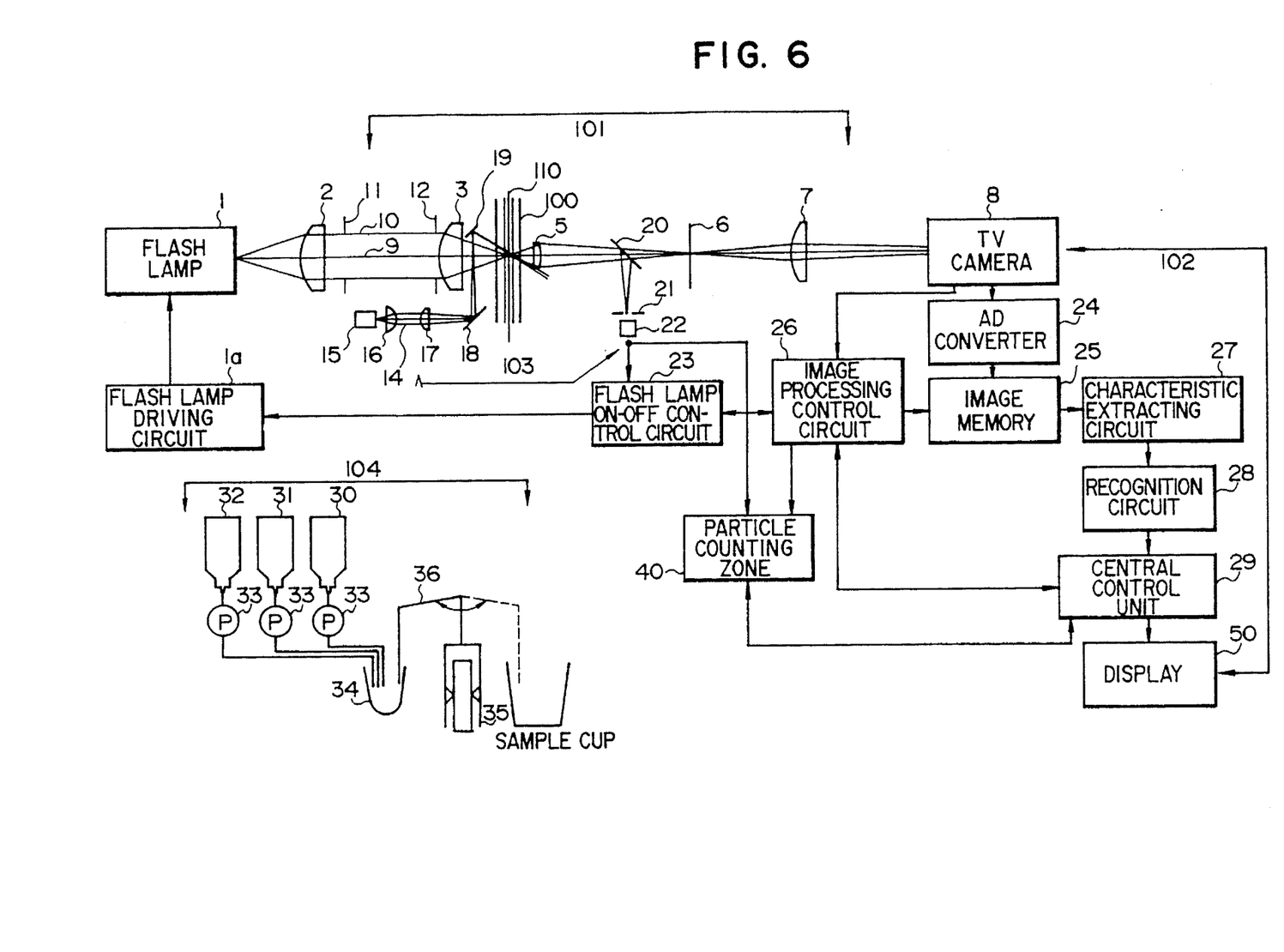
FIG. 6 shows the entire apparatus for image analysis of flow type stain particles according to the present invention.

One embodiment of the apparatus for image analysis of flow type stain particles according to the present invention is described below, by referring to FIGS. 6 and 7.

The the construction of the apparatus of the present invention for image analysis of flow type stain particles is first explained with reference to FIG. 6, which shows the entire structure. As shown in FIG. 6, the apparatus of the present invention for image analysis of flow type stain particles comprises a flow cell 100 for supplying a fluid sample in which particles are suspended, a means 101 for photographing images, a means 102 for analyzing particles, a means 103 for detecting particles and a means 104 for staining particles.

The photographing means 101 also has a function as a microscope and is equipped with a flash lamp 1 which is a pulse light source, a flash lamp driving circuit 1a which flashes the flash lamp 1, a field lens 2 which makes the pulse flux 10 from the flash lamp 1 parallel, a microscope condenser lens 3 which condenses the parallel pulse flux from the fieled lens 2 on to a fluid sample flow 110 in the flow cell 100, a microscope objective lens 5 which collects the pulse flux irradiated onto the fluid sample flow 110 to condense on an image forming position 6, a TV camera 8 which uptakes the image at the image forming position 6 projected through a projection lens 7 by an interlace system to covert the image into an electric image data signal, a field diaphragm 11 which restricts the width of pulse flux 10, and an opening diaphragm 12. As the TV camera 8 above, a CCD camera which has fewer afterimages is generally used.

The particle analysis means 102 comprises an AD converter 24 which converts the image data signal transferred through the TV camera 8 into a digital signal, an image memory 25 which memorizes data based on the signal from the AD converter 24 in a definite address, an image processing control circuit 26 which writes and reads data on and from the image memory, a characteristic extracting circuit 27 and a discrimination (recognition) circuit 28 which determine the count of particles and classify the particles by image processing based on the signal from the image memory 25, a particle counting zone 40 which determines the count of particles in a fluid sample, and a central control unit 29 which controls photographing conditions of the TV camera 8, conditions for a fluid sample flow in the flow cell 100 and the image processing control circuit 26, and memorizes the results of the image processing from the discrimination circuit 28, gives and takes data through the particle counting zone 40 and displays on a display zone 50.

The particle detection means 103 comprises a semiconductor laser 15 which is a light source for emitting laser light as a detection light, a collimator lens 16 which converts the laser light from the semiconductor laser 15 into a parallel laser flux 14, a cylindrical lens 17 which condenses only one direction of the laser flux from the collimator lens 16, a reflection mirror 18 which reflects the flux from the cylindrical lens 17, a micro-reflection mirror 19 which leads the laser flux from the reflection mirror 18 provided between the microscope condenser lens 3 and the flow cell 100 to a position near and upstream of an image uptake zone on the fluid sample flow 110, the microscope objective lens 5 which collects the laser lights of the aforesaid laser flux scattered by the particles, a beam splitter 20 which reflects the scattered lights thus condensed through the microscope objective lens 5, an optical detection circuit 22 which receives the light scattered from the beam splitter 20 through a diaphragm 21 and outputs an electric signal based on the strength, and the flash lamp on-off control circuit 23 which operates the flash lamp driving circuit 1a based on the electrical signal from the optical detection circuit 22. The microscope objective lens 5 is commonly employed also in the image photographing means 101.

The particle staining means 104 comprises a bottle 30 for holding a dyeing agent, a bottle 31 for holding a fixative agent, a sample syringe 35 which discharges the dyeing agent from a surfactant bottle 32 into a staining tank 34 through a dyeing agent discharge pump 33, and which also performs sampling of a fluid sample in which the particles are suspended, and a sample nozzle 36.

A sheath solution is supplied to the flow cell 100 together with a fluid sample to form a flow of the fluid sample enclosed into the sheath solution. The fluid sample flow 110 becomes a stable constant flow (sheath flow) which has a vertically flat cross section against the optic axis (optic axis of the microscope) 9 of the image photographing means 101. The fluid sample flow is thus sent downwards on the paper surface at the center of the flow cell 100. The flow rate of the fluid sample flow 110 is controlled under conditions set forth in the central control unit 29.

Figure 7:
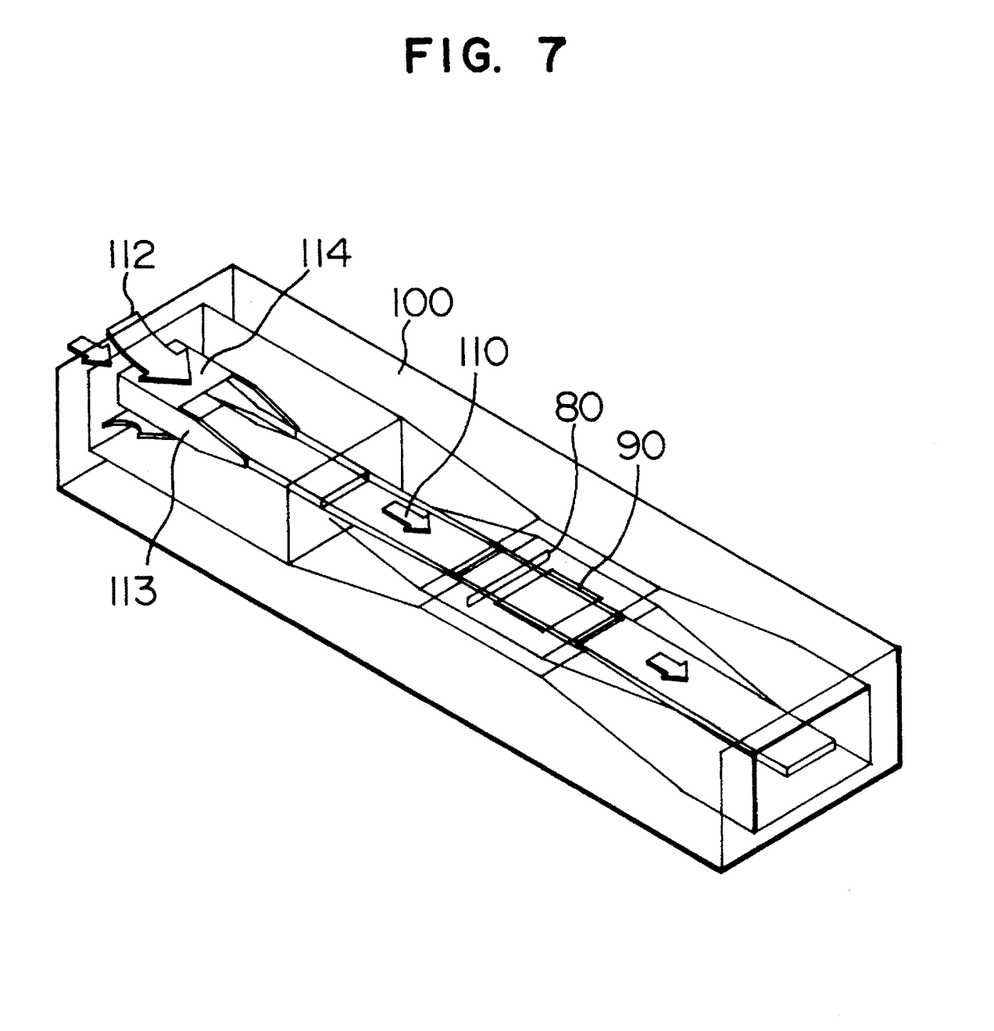
FIG. 7 is a perspective view showing a construction of a flow cell in the present invention.

The function of the flow cell 100 is explained by referring to the perspective view in FIG. 7 which shows the structure of the flow cell. The flow cell 100 is generally made of glass. The flow cell 100 has a sheath solution feeding port 112 for supplying the sheath solution to the flow cell and a fluid sample feeding port 114 for supplying the particle-containing sample to the flow cell. The sheath solution flows inside the flow cell so as to enclose the fluid sample to form a so-called laminar flow, whereby both the fluid sample and the sheath solution flow downstream without distorting the flow.

The inner shape of the flow cell is designed to form a condensed flow toward one direction of the laminar flow. As the result, a fluid sample flow is formed into a thin but wide and flat flow in the image photographing zone 90. The width of the flat flow is not affected by the condensed flow to maintain the width size equal to that of the fluid sample feeding port 114, in the vertical direction against the direction which receives the condensed flow. In actuality, however, a stable and constant width cannot be maintained due to complicated flows around the fluid sample feeding port 114 in different assay modes. Accordingly, a sample guide 113 is projected toward the sample feeding port to stabilize the width. The position on which the laser flux is condensed in the particle detection system is a particle detecting position 80.

A basic procedure operated by the apparatus for image analysis of flow type particles which has the construction described above is explained below.

Each reagent is discharged from the dyeing agent bottle 30 fixative agent bottle 31, and surface active agent bottle 32 to the staining tank 34 through the corresponding discharging pump 33. Then, a sample suspension in which particles are suspended is sampled through the sample syringe 35 and the sample nozzle 36, discharged into the staining tank 34, and stirred and allowed to stand there, whereby the particles are stained.

The semiconductor laser 15 oscillates continuously and always observes the particles in the sample to pass through the detection zone. As noted above, the laser flux from the semiconductor laser 15 is converted into a parallel laser flux 14 by the collimator lens 16, and is then condensed in one direction only by the cylindrical lens 17. The laser flux is reflected by the reflection mirror 18 and the micro-reflection mirror 19 and irradiated onto the sample flow 110 in the flow cell 100. The position irradiated is the particle detecting position 80, on which the laser flux is condensed through the cylindrical lens 17, and located near and upstream of the image photographing zone 90 on the sample flow 110.

When the particles to be detected pass across the laser flux, the laser flux is scattered by the particles. The scattered flux is reflected by the beam splitter 20 and received on the optical detection circuit 22, in which the scattered flux is converted into electric signals based on the flux intensity.

In the optical detection circuit 22, it is further determined if the detected electric signal is greater than a definite signal level; if the detected signal is greater than the definite signal level, it is regarded by the circuit that the particles to be image-processed have passed, and the detected signal is sent to the flash lamp on-off control circuit 23 and the particle counting zone 40. In the flash lamp on-off control circuit 23, the particles are sent to the flash lamp driving circuit 1a after a definite delay time determined by the distance between the particle detecting position and the image uptake zone and by a flow rate of the fluid sample, in such a manner that flash lamp 1 flashes to take a picture of the particles when the particles reach the position given in the image uptake zone of the TV camera 8. The delay time is extremely short because the distance between the particle detecting position and the image uptake zone is very short so that detection of the particles or analytical accuracy is not affected by a flow rate of the fluid sample or by a concentration of the particles. At the same time as the detected signal described above, a flash ready signal is sent from the flash lamp on-off control circuit 23 to control a flashing timing of the flash lamp based on the timing of the field signal by the interlace system. The detection signal in the flash lamp on-off control circuit 23 is sent to the image processing control circuit 26.

When the detection signal is sent to the flash lamp driving circuit 1a, the flash lamp driving circuit 1a flashes the flash lamp 1. The pulse light emerging from the flash lamp 1 propogates along the optic axis 9 of the microscope and passes through the field lens 2 to become parallel light. The parallel light is condensed through the microscope condenser lens 3 and the condensed light is irradiated onto the sample flow 110 in the flow cell 100. The width of the pulse flux 10 is restricted by the field diaphragm 11 and the opening diaphragm 12.

The pulse flux irradiated on the sample flow 110 in the flow cell 100 is gathered through the microscope objective lens 5 and forms an image at the image forming position 6. The image at the image forming position 6 is projected on the photographing surface of the TV camera 8 through the projection lens 7 and converted into an image data signal by the interlace system. By this procedure, still images of the particles are photographed. The conditions for photographing by the TV camera 8 are previously programmed in the central control unit 29, whereby the photographing behavior of the TV camera 8 is controlled.

In the apparatus for image analysis of flow type stain particles which is used for morphological classification of particles by photographing still images of the detected particles passing through the photographing zone in the flow cell and analyzing the particle images through image processing, the dyeing agent which is an embodiment of the present invention and a process for preparing the dyeing agent are explained below.

EXAMPLE 1

A dyeing agent which is an embodiment of the present invention and its preparation are shown below.

The dyeing agent for staining urinary sediments was prepared as follows. One volume of Solution I containing $3.2 \times 10^{-2}$ mol/l of Evans Blue was mixed with 1 volume of Solution II containing $6.3 \times 10^{-2}$ mol/l of Erythrosine, using as a solvent 1/15 mol/l of phosphate buffer (pH 6.8). After sodium azide as a fixative agent was further added to the mixture in a concentration of 0.1%, the mixture was filtered and stored in a light-resistant bottle.

The dyeing agent described above was blended with urinary sediments or with a urinary sample prior to centrifugation in a volume ratio of 1 to 10. Without causing coagulation of sugars, proteins and glycoproteins dissolved in the sample, the discernible components alone in the sample could be stained with good visual recognition.

EXAMPLE 2

A dyeing agent which is another embodiment of the present invention and its preparation and use are explained below.

The dyeing agent for staining urinary sediments was prepared as follows. One volume of Solution I containing $3.2 \times 10^{-2}$ mol/l of Evans Blue was mixed with 1 volume of Solution II containing $6.3 \times 10^{-2}$ mol/l of Phloxine, using as a solvent 1/15 mol/l of phosphate buffer (pH 6.8). After sodium azide as a fixative agent was further added to the mixture as in Example 1, the mixture was filtered and stored in a light-resistant bottle.

The dyeing agent described above was blended with urinary sediments or with a urinary sample prior to centrifugation in a volume ratio of 1 to 10. Without causing coagulation of sugars, proteins and glycoproteins dissolved in the sample, the discernible components alone in the sample could be stained with good visual recognition.

However, the Phloxine solution as the dyeing agent causes hemolysis of red blood cells. Therefore, glutaraldehyde was added in a concentration of 3% as a fixative agent for protecting red blood cells, whereby the discernible components were stabilized.

EXAMPLE 3

A dyeing agent which is a further embodiment of the present invention and its preparation and use are explained below.

The dyeing agent for staining urinary sediments was prepared as follows. One volume of Solution I containing $3.2 \times 10^{-2}$ mol/l of Evans Blue was mixed with 1 volume of Solution II containing $6.3 \times 10^{-2}$ mol/l of Eosine, using as a solvent 1/15 mol/l of phosphate buffer (pH 6.8). The fixative agent was further mixed with the above mixture as in Example 1. The resulting mixture was filtered and stored in a light-resistant bottle.

The dyeing agent described above was blended with urinary sediments or with a urinary sample prior to centrifugation in a volume ratio of 1 to 10. Without causing coagulation of sugars, proteins and glycoproteins dissolved in the sample, the discernible components alone in the sample could be stained with good visual recognition.

However, the Eosine solution as the dyeing agent nonuniformly stains various discernible components. In order to effect uniform staining, sodium dodecyl sulfate was further added as a surface active agent to the above mixture in a concentration of 0.1%, whereby stable staining was obtained. Further for the purpose of maintaining the shape, glutaraldehyde was added to the system in a concentration of 3%.

EXAMPLE 4

A dyeing agent for staining urinary sediments was prepared as follows. Solution I containing $2.0 \times 10^{-2}$ mol/l of Trypan Blue was mixed with Solution II containing $0.42 \times 10^{-1}$ mol/l of Erythrosine, in a ratio of 1:1, using as a solvent 1/15 mol/l of phosphate buffer (pH 6.8). The mixture was filtered and stored in a light-resistant bottle. The thus-obtained dyeing agent was set in the apparatus for image analysis of flow type stain particles.

The dyeing agent described above was blended with urinary sediments or with a urinary sample prior to centrifugation in a volume ratio of 1 to 10. Without causing coagulation of sugars, proteins and glycoproteins dissolved in the sample, the discernible components alone in the sample could be stained with good visual recognition.

EXAMPLE 5

A dyeing agent for staining urinary sediments was prepared as follows. One volume of Solution I containing $2.0 \times 10^{-2}$ mol/l of Trypan Blue was mixed with 1 volume of Solution II containing $0.42 \times 10^{-2}$ mol/l of Phloxine, using as a solvent 1/15 mol/l of phosphate buffer (pH 6.8). The mixture was filtered and stored in a light-resistant bottle. The thus-obtained dyeing agent was set in the apparatus for image analysis of flow type stain particles.

The dyeing agent described above was blended with urinary sediments or with a urinary sample prior to centrifugation in a volume ratio of 1 to 10. Without causing coagulation of sugars, proteins and glycoproteins dissolved in the sample, the discernible components alone in the sample could be stained with good visual recognition.

However, the Phloxine solution as the dyeing agent causes hemolysis of red blood cells. Therefore, glutaraldehyde was added in a concentration of 3% as a fixative agent for protecting the red blood cells, whereby the discernible components were stabilized.

EXAMPLE 6

A dyeing agent for staining urinary sediments was prepared as follows. One volume of Solution I containing $2.0 \times 10^{-2}$ mol/l of Trypan Blue was mixed with 1 volume of Solution II containing $0.42 \times 10^{-2}$ mol/l of Eosine, using as a solvent 1/15 mol/l of phosphate buffer (pH 6.8). The mixture was filtered and stored in a light-resistant bottle. The thus-obtained dyeing agent was set in the apparatus for image analysis of flow type stain particles.

The dyeing agent described above was blended with urinary sediments or with a urinary sample prior to centrifugation in a volume ratio of 1 to 10. Without causing coagulation of sugars, proteins and glycoproteins dissolved in the sample, the discernible components alone in the sample could be stained with good visual recognition.

However, the Eosine solution as the dyeing agent of the present invention non-uniformly stains various discernible components. In order to effect uniform staining, sodium dodecyl sulfate was further added as a surface active agent to the above mixture in a concentration of 0.1%, whereby stable staining was obtained. Further for the purpose of maintaining the shape, glutaraldehyde was added to the system in a concentration of 3%.

What is claimed is:

1. A dyeing agent for staining a biological sample, which comprises an azo dye and a xanthene dye suitable for supravital staining of cells and tissue, and a pH buffer, said azo and xanthene dyes being nonpolar molecular dyes which, upon blending, cause no agglutination or sedimentation of the dyes and which do not precipitate or agglutinate sugars, proteins or glycoproteins dissolved in said biological sample;

wherein the blended azo and xanthene dyes are suitable for staining at least two objects, to different respective degrees in color hue or in dyeing strength depending on the respective objects; and wherein the blended azo and xanthene dyes are suitable for staining respective components of a single object to different degrees in color hue or in dyeing strength.

2. A dyeing agent according to claim 1, wherein said azo dye is selected from the group consisting of Evans Blue and Trypan Blue.

3. A dyeing agent according to claim 1, wherein said xanthene dye is selected from the group consisting of Erythrosine, Phloxine and Eosin.

4. A dyeing agent according to claim 2, wherein said xanthene dye is selected from the group consisting of Erythrosine, Phloxine and Eosin.

5. A dyeing agent according to claim 4, wherein said pH buffer is selected from the group consisting of a phosphate buffer, a succinate buffer and a tris-acid buffer.

6. A dyeing agent according to claim 5, further comprising an antibacterial agent as a fixative agent.

7. A dyeing agent according to claim 6, wherein said antibacterial agent is selected from the group consisting of sodium azide, para-hydroxyphenylacetic acid, dehydroacetic acid and ethylenediaminetetraacetic acid.

8. A dyeing agent obtained by mixing one volume of about 0.2 to $10.0 \times 10^{-2}$ mol/l of Evans Blue or Trypan Blue with about 0.5 to 2.0 volumes of about 0.2 to $10.0 \times 10^{-2}$ mol/l of Erythrosine; and adjusting a pH of the system to 5.7 to 7.9 using 1/30 to 1/5 mols/l of a solvent selected from the group consisting of a phosphate buffer, a succinate buffer and a tris-acid buffer.

9. A dyeing agent according to claim 1, further comprising a fixative agent.

10. A dyeing agent according to claim 9 obtained by mixing one volume of about 0.2 to $10.0 \times 10^{-2}$ mol/l of Evans Blue or Trypan Blue as the azo dye with about 0.5 to 2.0 volumes of about 0.2 to $10.0 \times 10^{-2}$ mol/l of Phloxine as the xanthene dye; adjusting a pH of the system to 5.7 to 7.9 using 1/30 to 1/5 mols/l of a solvent selected from the group consisting of a phosphate buffer, a succinate buffer and a tris-acid buffer; and further adding an agent selected from the group consisting of glutaraldehyde, formaldehyde and paraformaldehyde as the fixative agent to the mixture in a concentration of 0.02 to 5.0%.

11. A dyeing agent according to claim 9, further comprising a surface active agent.

12. A dyeing agent according to claim 11, which is obtained by mixing one volume of about 0.2 to $10.0 \times 10^{-2}$ mol/l of Evans Blue or Trypan Blue as the azo dye with about 0.5 to 2.0 volumes of about 0.2 to $10.0 \times 10^{-2}$ mol/l of Eosine as the xanthene dye; adjusting a pH of the system to 5.7 to 7.9 using 1/30 to 1/5 mols/l of a solvent selected from the group consisting of a phosphate buffer, a succinate buffer and a tris-acid buffer; and further adding an agent selected from the group consisting of glutaraldehyde, formaldehyde and paraformaldehyde as the fixative agent to the mixture in a concentration of 0.02 to 5.0%, and sodium dodecyl sulfate as the surface active agent in a concentration of 0.01 to 0.5%.

13. A method for staining discernible urinary sediments in urine, comprising the step of using a dyeing agent according to claim 7.

14. A dyeing agent according to claim 8, wherein the dyeing agent is further obtained by mixing with the mixture one member selected from the group consisting of sodium azide, parahydroxyphenylacetic acid, dehydroacetic acid and ethylenediaminetetraacetic acid in a concentration of 0.01 to 1.0%.

15. A dyeing agent according to claim 10, wherein the dyeing agent is further obtained by mixing with the mixture one member selected from the group consisting of sodium azide, para-hydroxyphenylacetic acid, dehydroacetic acid and ethylenediaminetetraacetic acid in a concentration of 0.01 to 1.0%.

16. A dyeing agent according to claim 12, wherein the dyeing agent is further obtained by mixing with the mixture one member selected from the group consisting of sodium azide, para-hydroxyphenylacetic acid, dehydroacetic acid and ethylenediaminetetraacetic acid in a concentration of 0.01 to 1.0%.

17. A dyeing agent for staining a biological sample, obtained by mixing one volume of about 0.2 to $10.0 \times 10^{-2}$ mol/l of Evans Blue or Trypan Blue as a first dye with about 0.5 to 2.0 volumes of about 0.2 to $10.0 \times 10^{-2}$ mol/l of Phloxine as a second dye; adjusting a pH of the system to 5.7 to 7.9 using 1/30 to 1/5 mols/l of a solvent selected from the group consisting of a phosphate buffer, a succinate buffer and a tris-acid buffer; and further adding a fixative agent selected from the group consisting of glutaraldehyde, formaldehyde and paraformaldehyde to the mixture in a concentration of 0.02 to 5.0%.

18. A dyeing agent according to claim 17, further comprising a surface active agent.

19. A dyeing agent according to claim 17,
    wherein upon mixing the first and second dyes, the first and second dyes cause no agglutination or sedimentation of the first and second dyes, and do not precipitate or agglutinate sugars, proteins or glycoproteins dissolved in said biological sample;
    wherein the mixed first and second dyes are suitable for staining at least two objects to different respective degrees in color hue or in dyeing strength depending on the respective objects; and
    wherein the mixed first and second dyes are suitable for staining respective components of a single object to different degrees in color hue or in dyeing strength.

20. A dyeing agent according to claim 17, wherein the dyeing agent is further obtained by mixing with the mixture one member selected from the group consisting of sodium azide, para-hydroxyphenylacetic acid, dehydroacetic acid and ethylenediaminetetraacetic acid in a concentration of 0.01 to 1.0%.

21. A dyeing agent for staining a biological sample, obtained by mixing one volume of about 0.2 to $10.0 \times 10^{-2}$ mol/l of Evans Blue or Trypan Blue as a first dye with about 0.5 to 2.0 volumes of about 0.2 to $10.0 \times 10^{-2}$ mol/l of Eosine as a second dye; adjusting a pH of the system to 5.7 to 7.9 using 1/30 to 1/5 mols/l of a solvent selected from the group consisting of a phosphate buffer, a succinate buffer and a tris-acid buffer; and further adding a fixative agent selected from the group consisting of glutaraldehyde, formaldehyde and paraformaldehyde to the mixture in a concentration of 0.02 to 5.0%, and sodium dodecyl sulfate as a surface active agent in a concentration of 0.01 to 0.5%.

22. A dyeing agent according to claim 21,
    wherein upon mixing the first and second dyes, the first and second dyes cause no agglutination or sedimentation of the first and second dyes and do not precipitate or agglutinate sugars, proteins or glycoproteins dissolved in said biological sample;
    wherein the mixed first and second dyes are suitable for staining at least two objects to different respective degrees in color hue or in dyeing strength depending on the respective objects; and
    wherein the mixed first and second dyes are suitable for staining respective components of a single object to different degrees in color hue or in dyeing strength.

23. A dyeing agent according to claim 21, wherein the dyeing agent is further obtained by mixing with the mixture one member selected from the group consisting of sodium azide, para-hydroxyphenylacetic acid, dehydroacetic acid and ethylenediaminetetraacetic acid in a concentration of 0.01 to 1.0%.

\* \* \* \* \*